United States Patent [19]
Hirschmann et al.

[11] Patent Number: 6,001,960
[45] Date of Patent: *Dec. 14, 1999

[54] SYNTHETIC SOMATOSTATIN MIMICS

[75] Inventors: Ralph F. Hirschmann, Blue Bell, Pa.; Rolando A. Spanevello, Rosario, Argentina; Ruth F. Nutt, Green Lane, Pa.

[73] Assignee: The Trustees of the University of Pennsylvania, Philadelphia, Pa.

[ * ] Notice: This patent is subject to a terminal disclaimer.

[21] Appl. No.: 08/997,263

[22] Filed: Dec. 23, 1997

Related U.S. Application Data

[63] Continuation of application No. 08/338,890, Nov. 14, 1994, Pat. No. 5,700,905, which is a continuation of application No. 08/188,594, Jan. 28, 1994, abandoned, which is a continuation of application No. 07/938,803, Sep. 1, 1992, abandoned.

[51] Int. Cl.$^6$ ........................... A61K 38/12; A61K 38/31; C07K 7/64; C07K 14/655
[52] U.S. Cl. ............................... 530/311; 514/11; 930/160
[58] Field of Search ...................................... 530/311, 317, 530/328; 514/11, 14, 17; 930/160, 270, 280, DIG. 533, DIG. 534

[56] References Cited

U.S. PATENT DOCUMENTS

| | | | |
|---|---|---|---|
| 4,162,248 | 7/1979 | Strachan et al. | 530/311 |
| 4,235,886 | 11/1980 | Freidinger et al. | 514/11 |
| 4,427,661 | 1/1984 | Curley et al. | 530/311 |
| 4,486,415 | 12/1984 | Freidinger et al. | 530/311 |
| 4,585,755 | 4/1986 | Morgan et al. | 514/11 |
| 4,621,073 | 11/1986 | Friedrick et al. | 530/311 |
| 4,703,034 | 10/1987 | Freidinger et al. | 530/311 |
| 4,798,821 | 1/1989 | Hartmann | 514/9 |
| 5,145,837 | 9/1992 | Feyen et al. | 514/16 |
| 5,700,905 | 12/1997 | Hirschman et al. | 530/311 |

FOREIGN PATENT DOCUMENTS

| | | | |
|---|---|---|---|
| 0000053 | 12/1978 | European Pat. Off. | 530/311 |
| 0248209 | 12/1987 | European Pat. Off. | 530/311 |

OTHER PUBLICATIONS

Spanevello et al, Tetrahedron Lett., vol. 32(36),pp. 4675–8, (1991).
Nutt et al, Int. J. Pept. Protei Res. 21(1), pp. 66–73, (1983).
The Condens Chemical Dictionary, 10$^{th}$ ed, p. 90 (1981).
Atherton, E. et al., *The Peptides*, Gross and Meienhofer, Eds., Academic Press, New York, 1983, vol. 9 pp. 1–38.
Bethell, G. et al., "A Novel Method of Activation of Cross–linked Agaroses with 1,1'–Carbonyldiimidazole Which gives a Matrix for Affinity Chromatography Devoid of Additional Charged Groups", *J. Biol. Chem.* 1979, 259, 2572–2574.
Bosshard, H.–R. et al., "A New Method for the Detection of Racemization During Peptide Synthesis; Stereoselective Hydrolysis of Diastereomeric Peptides by Leucine Aminopeptidase", *Helv Chim. Acta* 1973, 56, 717–723.
Cuatrecasas et al., "Selective Enzyme Purification by Affinity Chromatography", *PNAS USA* 1968, 61, 636–643.
Greene and Wuts, *Protective Groups in Organic Synthesis*, 2d Edition, John Wiley & Sons, New York, 1991.
He et al., "Purification of a Putative Brain Somatostatin Receptor", *PNAS USA* 1989, 86, 1480–1484.
Masui, Y. et al., "The Modification of Tryptophyl Residues During the Acidolytic Cleavage of Boc–groups. I. Studies with Boc–Tryptophan", *Bull. Chem. Soc. Jpn.* 1980, 53, 464–468.
Mendelson, W. et al., "Simplified Method for O–Alkylation of N–Protected Tyrosines", *J. Org. Chem.* 1983, 48, 4127–4129.
Raynor, K. et al., "Analogs of Somatostatin selectively label Distinct Subtypes of Somatostatin Receptors in Rat Brain", *J. Pharmacol. Exp. Ther.* 1989, 251, 510–517.
Tung et al., "Bis(2–oxo–3–oxazolidinyl) phosphinic Chloride (1) as a Coupling Reagent for N–Alkyl Amino Acids", *J. Amer. Chem. Soc.* 1985, 107, 4342–4343.
Van der Auwera, C. et al., "Racemization During Peptide Coupling with N,N'–bis(2–oxo–3–oxazolidinyl) Phosphinic Chloride (BOP–Cl)", *Int. J. Peptide Res.* 1987, 29, 464–471.
Veber, D. et al. "Isonicotinyloxycarbonyl, a Novel Amino Protecting Group for Peptide Synthesis", *J. Org. Chem.* 1977, 42, 3286–3288.
Veber, D. et al., "A Super Active Cyclic Hexapeptide Analog of Somatostatin", *Life Sciences* 1984, 34, 1371–1378.
Veber, D. et al., "A Potent Cyclic Hexapeptide Analogue of Somatostatin", *Nature* 1981, 292, 55–58.
Brady, S. et al., "Large–Scale Synthesis of a Cyclic Hexapeptide Analogue of Somatostatin", *J. Org. Chem.* 1987, 52, 764–769.
Van der Auwera and Anteunis, "N, N–bis(2–oxo–3–oxazolidiniyl) Phosphinic Chloride (BOP–Cl); a Superb Reagent for Coupling at and with Iminoacid Residues", *Int. J. Peptide Protein Res.* 1987, 29, 574–588.
Yajima, H. et al., *The Peptides*, Gross and Meienhofer, Eds., Academic Press, New York, 1983, vol. 5 pp. 65–109.

*Primary Examiner*—Jeffrey E. Russel
*Attorney, Agent, or Firm*—Woodcock Washburn Kurtz Mackiewicz & Norris

[57] ABSTRACT

Relatively small cyclic peptides that mimic the biological and/or chemical activity of larger cyclic peptide such as somatostatin, as well as synthetic methods therefor. In certain embodiments, cyclic peptides of the invention have structure:

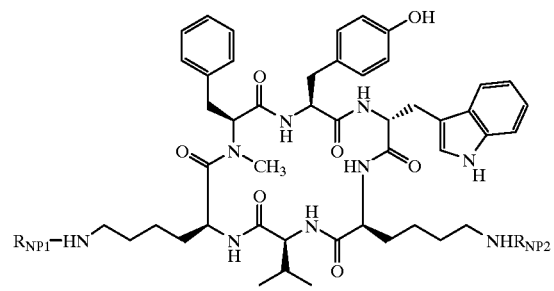

wherein $R_{NP1}$ is H, an amine protecting group, or a solid support and $R_{NP2}$ is H or an amine protecting group.

22 Claims, No Drawings

SYNTHETIC SOMATOSTATIN MIMICS

This application is a continuation of application Ser. No. 08/338,890 filed Nov. 14, 1994, now U.S. Pat. No. 5,700,905, which is a continuation of 08/188,594 filed on Jan. 28, 1994, now abandoned, which is a continuation of 07/938,803 which was filed on Sep. 1, 1992, now abandoned.

FIELD OF THE INVENTION

This invention relates to relatively small cyclic peptides that mimic the biological and/or chemical activity of larger cyclic peptides such as somatostatin.

BACKGROUND OF THE INVENTION

Peptides are implicated in a wide variety of biochemical processes in humans and other mammals. The design of peptide mimics which are resistant to degradation by proteolytic enzymes has become of increasing interest to peptide chemists. A primary goal has been to reduce the susceptibility of mimics to cleavage aid inactivation by peptidases.

Somatostatin (SRIF; somatotropin release inhibiting factor), a cyclic tetradecapeptide, was first isolated from bovine hypothalamus and characterized as an inhibitor of growth hormone secretion. SRIF receptors have been found not only on pituitary cells but also in the brain, on gastric or pancreatic cells, and elsewhere. This has stimulated interest in the isolation of SRIF receptors by affinity chromatography in amount sufficient for partial sequence determination. For example, He, et al, *Proc. Natl. Acad. Sci. (USA)*, 1989, 86, 1480, have described the use of D-Trp$^8$ SRIF as an affinity ligand.

The bioactive conformation of SRIF is believed to include a β-turn involving residues 7–10 (Phe$^7$-Trp$^8$-Lys$^9$-Thr$^{10}$) (SEQ ID NO:1). These four amino acids have been shown to be necessary and sufficient for receptor recognition and activation, so long as they are held in the proper orientation. Somatostatin accomplishes this proper orientation through its ten remaining amino acids and the cystine bridge contained therein. In a number of active cyclic hexapeptide analogs for somatostatin, proper orientation of the four amino acids is maintained via dipeptide segments. For example, Veber and Hirschmann, et al., *Life Sciences*, 1984, 34, 1371 and *Nature*, 1981, 292 have reported that cyclic hexapeptides typified by cyclo (Pro-Phe-D-Trp-Lys-Thr-Phe) are potent mimics of somatostatin.

OBJECTS OF THE INVENTION

It is one object of the present invention to provide cyclic peptides that mimic the biological and/or chemical activity of larger cyclic peptides.

It is another object to provide cyclic peptides that are chemically more stable than naturally-occurring cyclic peptides, particularly under conditions such as found in the human body.

It is yet another object to provide cyclic peptides that can be used as affinity ligands for G-protein-linked receptors, particularly the-somatostatin receptor.

It is a further object of the invention to provide simple yet efficient methods for synthesizing cyclic peptides.

SUMMARY OF THE INVENTION

These and other objects are accomplished by the present invention, which provides relatively stable, cyclic peptides that bind G-protein linked receptors such as the somatostatin receptor.

In certain embodiments, cyclic peptides of the invention have structure (1):

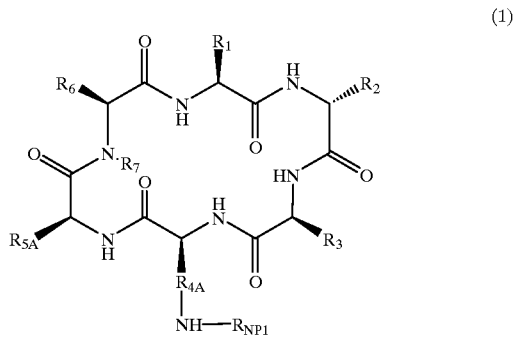

(1)

wherein:
$R_1$, $R_2$, $R_3$, $R_{5A}$, and $R_6$ are, independently, $(CH_2)_x$—$R_X$ where x is 0 to about 5 and $R_X$ is:
  alkyl or alkenyl having from about 1 to about 5 carbon atoms, from 0 to about 3 oxygen atoms, from 0 to about 3 nitrogen atoms, and from 0 to about 3 sulfur atoms; and
  aryl having 6 to about 14 carbon atoms, from 0 to about 4 oxygen atoms, from 0 to about 4 nitrogen atoms, and from 0 to about 4 sulfur atoms; or
  $NHR_{NP2}$ where $R_{NP2}$ is H or an amine protecting group;
$R_{4A}$ is alkyl or alkenyl having from about 1 to about 14 carbon atoms;
$R_{NP1}$ is H, an amine protecting group, or a solid support; and
$R_7$ is H or alkyl having about 1 to about 3 carbon atoms; or
$R_6$ and $R_7$ together form a heterocyclic ring having about 4 to about 8 atoms.

In other embodiments, the cyclic peptides of the invention have structure (2):

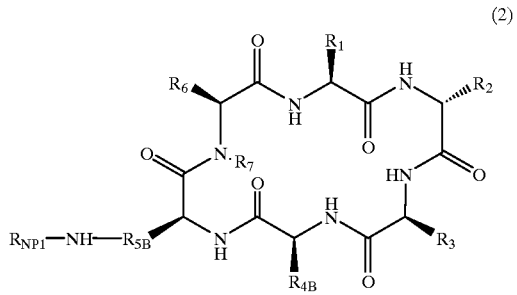

(2)

wherein:
$R_1$, $R_2$, $R_3$, $R_{4B}$, and $R_6$ are, independently, $(CH_2)_x$—$R_X$ where x is 0 to about 5 and $R_X$ is:
  alkyl or alkenyl having from about 1 to about 5 carbon atoms, from 0 to about 3 oxygen atoms, from 0 to about 3 nitrogen atoms, and from 0 to about 3 sulfur atoms; and
  aryl having about 3 to about 14 carbon atoms, from 0 to about 4 oxygen atoms, from 0 to about 4 nitrogen atoms, and from 0 to about 4 sulfur atoms; or
  $NHR_{NP2}$ where $R_{NP2}$ is H or an amine protecting group;
$R_{5B}$ is alkyl or alkenyl having from about 1 to about 14 carbon atoms;

$R_{NP1}$ is H, an amine protecting group, or a solid support; and $R_7$ is H or alkyl having about 1 to about 3 carbon atoms; or $R_6$ and $R_7$ together form a heterocyclic ring having about 4 to about 8 atoms.

The present invention also provides synthetic methods for these and other cyclic peptides, as well as intermediates useful in such methods. For example, the invention provides methods for preparing cyclic peptides having structure (3):

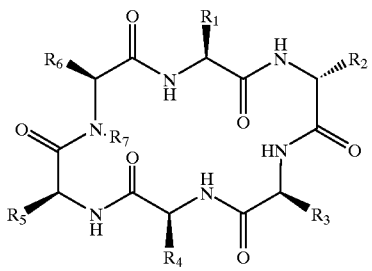

(3)

wherein:

$R_1$–$R_6$ are, independently, $(CH_2)_x$—$R_X$ where x is 0 to about 5, and $R_X$ is:

alkyl or alkenyl having from about 1 to about 5 carbon atoms, from 0 to about 3 oxygen atoms, from 0 to about 3 nitrogen atoms, and from 0 to about 3 sulfur atoms; and aryl having about 3 to about 14 carbon atoms, from 0 to about 4 oxygen atoms, from 0 to about 4 nitrogen atoms, and from 0 to about 4 sulfur atoms; or $NHR_{NP2}$ where $R_{NP2}$ is H or an amine protecting group;

at least one of $R_4$–$R_6$ is $R_Q$—NH—$R_{NP1}$ wherein $R_Q$ is alkyl or alkenyl having from about 1 to about 14 carbon atoms and $R_{NP1}$ is H; and $R_7$ is H or alkyl having about 1 to about 3 carbon atoms; or $R_6$ and $R_7$ together form a heterocyclic ring having about 4 to about 8 atoms;

These methods comprise the steps of providing a first compound having structure (4):

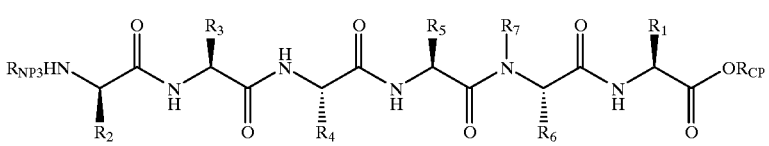

(4)

wherein $R_{NP1}$, $R_{NP2}$, and $R_{NP3}$ are amine protecting groups, $R_{CP}$ is a carboxyl protecting group, and $R_{NP3}$ and $R_{CP}$ can be removed in the presence of $R_{NP1}$ and $R_{NP2}$. In accordance with the invention, compounds having structure (4) are cyclized and exposed to conditions effective to remove the $R_{NP1}$ group. Cyclic peptides thus prepared can be attached to a solid support via the resultant free amine group.

DETAILED DESCRIPTION OF THE INVENTION

In preferred embodiments, cyclic peptides according to the present invention have structure (1) or structure (2):

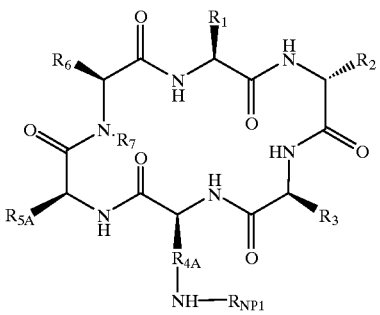

(1)

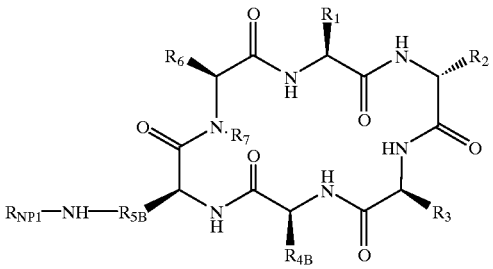

(2)

wherein:

$R_1$, $R_2$, $R_3$, $R_{4B}$, $R_{5A}$, and $R_6$ are, independently, $(CH_2)_x$—$R_X$ where x is 0 to about 5 and $R_X$ is:

alkyl or alkenyl having from about 1 to about 5 carbon atoms, from 0 to about 3 oxygen atoms, from 0 to about 3 nitrogen atoms, and from 0 to about 3 sulfur atoms; and aryl having about 3 to about 14 carbon atoms, from 0 to about 4 oxygen atoms, from 0 to about 4 nitrogen atoms, and from 0 to about 4 sulfur atoms;

$NHR_{NP2}$ where $R_{NP2}$ is H or an amine protecting group;

$R_{4A}$ and $R_{5B}$ are alkyl or alkenyl having from about 1 to about 14 carbon atoms;

$R_{NP1}$ is H, an amine protecting group, or a solid support; and $R_7$ is H or alkyl having about 1 to about 3 carbon atoms; or $R_6$ and $R_7$ together form a heterocyclic ring having about 4 to about 8 atoms.

Alkyl groups of the invention include but are not limited to straight chain, branched chain, and cyclic hydrocarbons such as methyl, ethyl, propyl, butyl, pentyl, isopropyl, 2-butyl, isobutyl, 2-methylbutyl, and isopentyl moieties, as well as heteroatomic derivatives thereof. Alkenyl groups from such alkyl groups, including but not limited to vinyl and allyl moieties. Aryl groups include but are not limited to aromatic and heteroaromatic moieties such as phenyl, tolyl, benzyl, naplithyl, anthracyl, phenanthryl, xylyl, hydroxyphenyl, indole, imidazole, tetrazole, and triazole moieties, including lalogenated derivatives thereof. Suitable heterocyclic groups include but are not limited to pyrrolidine and piperidine moieties.

Protecting groups are known per se as chemical functional groups that can be selectively appended to and removed from functionality, such as amine groups, present in a chemical compound to render such functionality inert to chemical reaction conditions to which the compound is exposed. See, e.g., Greene and Wuts, *Protective Groups in Organic Synthesis*, 2d edition, John Wiley & Sons, New York, 1991. Numerous amine protecting groups are known in the art, including the benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber and Hirschmann, et al., *J. Org. Chem.*, 1977, 42, 3286 and Atherton, et al., *The Peptides*, Gross and Meienhofer, Eds, Academic Press; New York, 1983; Vol. 9 pp. 1–38). For example, it is known that the Boc group can protect an amine group from base and from reducing conditions but that it can be removed with acid.

The cyclic peptides of the present invention can be attached to a solid support for use as, for example, affinity ligands. Such attachment preferably is effected through a free amine group such as the amine group appended to the $R_{4A}$ group of structure (1) or the amine group appended to the $R_{5B}$ group of structure (2). Suitable solid supports are well known to persons skilled in the arts of chromatography and/or solid phase synthesis. (See, e.g., He, et al., *Proc. Natl. Acad. Sci.* (*USA*), 1989, 86, 1480; Cuatrecasas, et al., *Proc. Natl. Acad. Sci.* (*USA*), 1968, 61, 636; and Bethell, et al., *J. Biol. Chem.*, 1979, 259, 2572.) Useful supports include PAM resins, Merrifield peptide resins, and polyamide peptide resins. A preferred solid support is Affi-gel 10, which is commercially available from Bio-Rad (Richmond, Calif.).

Preferred cyclic peptides of the invention are those wherein $R_1$–$R_7$ are derived from the side chains of naturally-occurring amino acids. Exemplary side chains are provided in Table 1.

TABLE 1

CH$_3$—
HO—CH$_2$—
C$_6$H$_5$—CH$_2$—
HO—C$_6$H$_5$—CH$_2$—

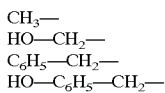

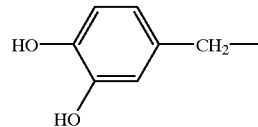

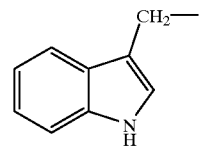

TABLE 1-continued

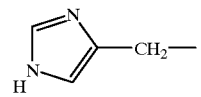

HS—CH$_2$—
HO$_2$C—CH(NH$_2$)—CH$_2$—S—S—CH$_2$—
CH$_3$—CH$_2$—
CH$_3$—S—CH$_2$—CH$_2$—
CH$_3$—CH$_2$—S—CH$_2$—CH$_2$—HO—CH—CH$_2$—
CH$_3$—CH(OH)—
HO$_2$C—CH$_2$—NH$_2$C(O)—CH$_2$—

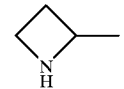

HO$_2$C—CH$_2$—CH$_2$—
NH$_2$C(O)—CH$_2$—CH$_2$—
(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—
H$_2$N—C(NH)—NH—CH$_2$—CH$_2$—CH$_2$—
H$_2$N—C(O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

Preferred cyclic peptides are those wherein $R_1$ is hydroxybenzyl, $R_2$ is —CH$_2$-(indole), and/or $R_3$ is —(CH$_2$)$_4$NHR$_{NP2}$, wherein R$_{NP2}$ is H or an Fmoc group. Cyclic peptides having structures (5) and (6) are particularly preferred.

(5)

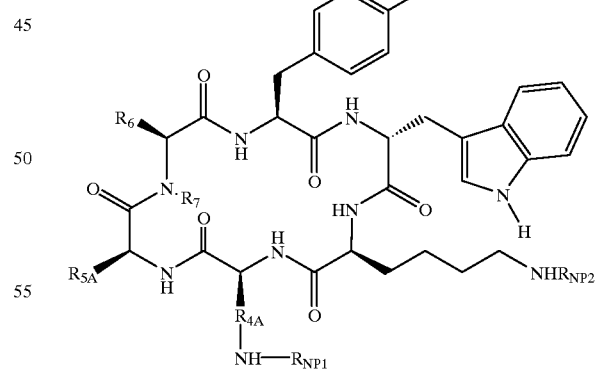

(6)
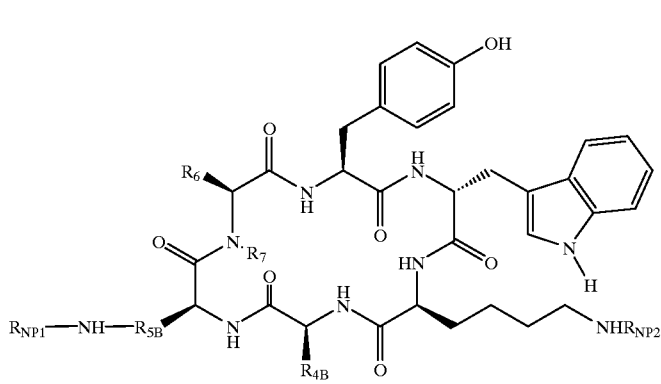
Preferably, $R_{4A}$ is —$(CH_2)_3NH$—, $R_{5B}$ is —$(CH_2)_4NH$—, and $R_{NP1}$ is H or an isonicotinyloxycarbonyl protecting group. Cyclic peptides having structure (7) or structure (8) are particularly preferred.
(7)
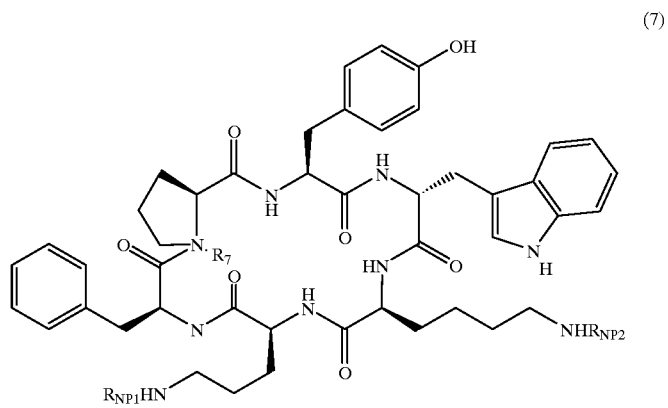
(SEQ ID NO:2)
(8)
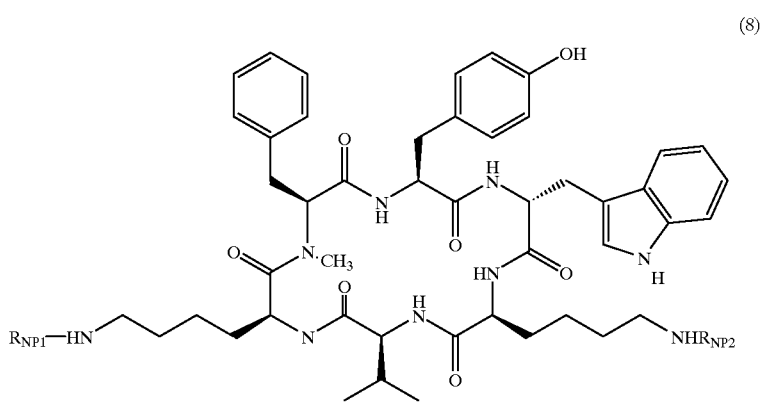
(SEQ ID NO:5)
These and other cyclic peptides are prepared through cyclization of suitably protected linear peptides such as structures (9) and (10):

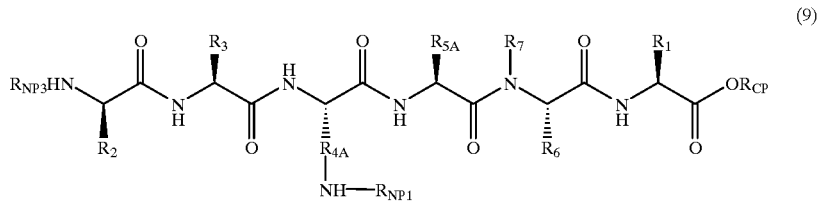
(9)
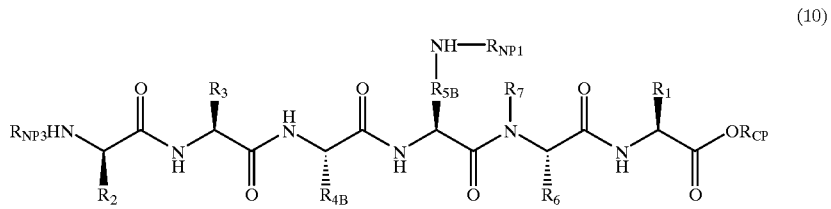
(10)
wherein $R_{CP}$ is a carboxyl protecting group, $R_{HP}$ is a hydroxyl protecting group, and $R_{NP1}$, $R_{NP2}$, and $R_{NP3}$ are amine protecting groups. For example, cyclic peptides having structures (1) and (2) can be prepared by processes that include cyclizing synthetic intermediates (11) and (12), respectively.
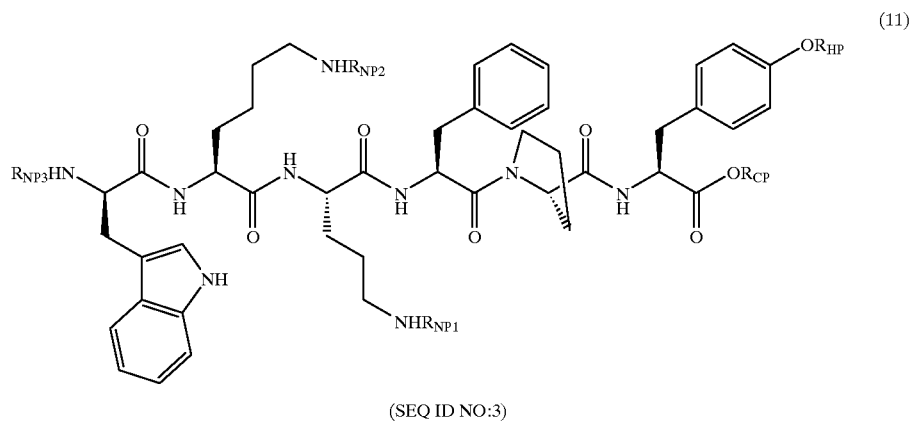
(11)
(SEQ ID NO:3)
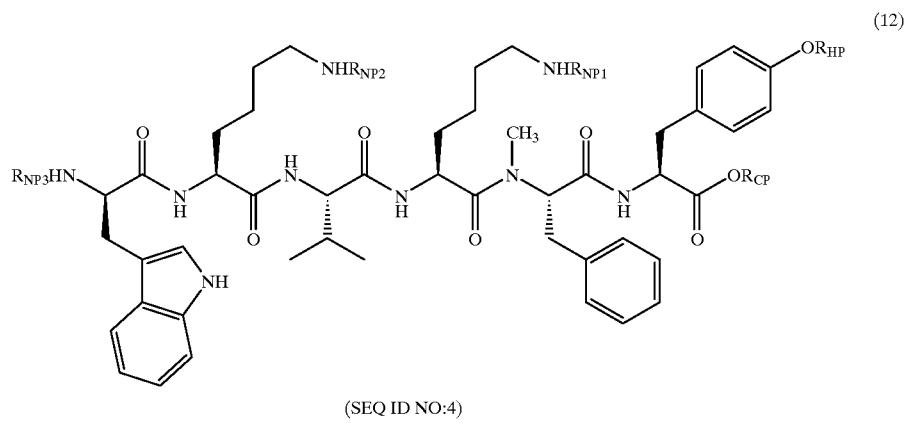
(12)
(SEQ ID NO:4)

Carboxyl protecting groups are known per se as chemical functional groups that can be selectively appended to and removed from carboxyl functionality present in a chemical compound to render such functionality inert to chemical reaction conditions to which the compound is exposed. Numerous carboxyl protecting groups are known in the art, including trimethylsilyl, 2-(trimethylsilyl)ethyl, 2,2,2-trichloroethyl, t-butyldimethylsilyl, p-methoxybenzyl, t-butyl, and 2-methylthioethyl groups. (See, e.g., Greene and Wuts, *Protective Groups in Organic Synthesis*, 2d edition, John Wiley & Sons, New York, 1991, pp. 224–276.) By analogy, hydroxyl protecting groups can be appended to and removed from hydroxyl groups. Representative hydroxyl groups include 2-chlorobenzyl, 2,6-dichlorobenzyl, cyclohexyl, t-butyl, o-nitrobenzyl, methylthiomethyl, allyl, t-butyldimethylsilyl, and t-butyldiphenylsilyl groups. (See, e.g., Greene and Wuts, *Protective Groups in Organic Synthesis*, 2d edition, John Wiley & Sons, New York, 1991, pp. 1–179.)

The respective amine, acid, and hydroxyl protecting groups should be carefully selected such that hydroxyl protecting group $R_{HP}$, carboxyl protecting group $R_{CP}$, and amine protecting group $R_{NP3}$ can be removed in the presence of amine protecting groups $R_{NP1}$ and $R_{NP2}$. Also, it should be possible to remove the $R_{NP1}$ group in the presence of the $R_{NP2}$ group. In preferred embodiments, $R_{HP}$, $R_{CP}$, and $R_{NP3}$ are acid labile, $R_{NP1}$ is stable to acid but labile under reducing conditions, and $R_{NP2}$ is stable to acid and reducing conditions but labile to base. More preferably, $R_{HP}$ is 2-chlorobenzyl, $R_{CP}$ is 2-(trimethylsilyl)ethyl, $R_{NP3}$ is a Boc group, $R_{NP1}$ is an i-Noc group, and $R_{NP3}$ is a Fmoc group.

Additional objects, advantages, and novel features of this invention will become apparent to those skilled in the art upon examination of the following examples thereof, which are not intended to be limiting.

EXAMPLE 1

Linear peptides having structures (11) and (12) [$R_{CP}$=2-(trimethylsilyl)ethyl, $R_{HP}$=2-chlorobenzyl, $R_{NP1}$=i-Noc, $R_{NP2}$=Fmoc, $R_{NP3}$=Boc] were synthesized by solution chemistry from $N^{\alpha}$-Boc-O-2-chlorobenzyl-Tyr[Boc-Tyr(Cl-Bzl] generally in accordance with Mendelson, et al.; *J. Org. Chem.* 1983, 48, 4127. The latter was converted into the corresponding 2-(trimethylsilyl)ethyl ester. In elaborating the linear peptide, the $N^{\alpha}$-Boc amino acids were coupled using N,N'-dicyclohexylcarbodiimide and 1-hydroxybenzotriazole in methylene chloride in the presence of N-methyl morpholine generally in accordance with Bosshard, et al., *Helv. Chim. Acta.*, 1973, 56, 717. N,N-Bis(2-oxo-3-oxazolidinyl)phosphinic chloride was used as a coupling reagent when the N-Me-Phe was involved in amide bond formation. (see, e.g., Tung, et al., *J. Amer. Chem. Soc.*, 1985, 107, 4342;. van der Auwera, et al., *Int. J. Peptide Res.*, 1987, 29, 574 and *Int. J. Peptide Res.* 1987, 29, 464). Boc groups were removed with TFA generally in accordance with Masui, et al., *Bull. Chem. Soc. Jpn.*, 1980, 53, 464.

$N^{\alpha}$-Boc-$N^{\delta}$-iNoc-Orn, $N^{\alpha}$-Boc-$N^{\epsilon}$-iNoc-Lys$^{11}$ and $N^{\alpha}$-Boc-$N^{\epsilon}$-Fmoc-Lys were prepared from the corresponding $N^{\alpha}$-Boc amino acids using procedures described in the literature. (see, e.g., Veber and Hirschmann, et al., *J. Org. Chem.* 1977, 42, 3286; Bosshard, et al., *Helv. Chim. Acta.*, 1973, 56, 717). N-Tetrabutyl ammonium fluoride could not be employed for the selective removal of the 2-(trimethylsilyl) ethyl ester because it is sufficiently basic to cleave the Fmoc group at Lys. Further, both the HF-pyridine complex and HF in acetonitrile failed to remove the ester protecting group.

Methanesulfonic acid in TFA removed the C-terminal ester, the N-terminal Boc group as well as the 2-chlorobenzyl ether to afford linear peptides having structures (11) and (12) [$R_{CP}$=$R_{HP}$ $R_{NP3}$=H, $R_{NP1}$=i-Noc, $R_{NP2}$=Fmoc]. (see, e.g., Yajima, et al., The Peptides, Gross and Meienhofer, Eds, Academic Press; New York, 1983; Vol. 5 pp. 65–109 and references cited therein). The crude material was directly cyclized using diphenylphosphoryl azide (DPPA) and solid NaHCO$_3$ in anhydrous dimethylformanide (DMF) under high dilution conditions, yielding the cyclic peptides having structures (7) and (8) [$R_{NP1}$=i-Noc, $R_{NP2}$=Fmoc]. (see, e.g., Brady, et al., *J. Org. Chem.* 1987, 52, 764). Aliquots of the crude materials and final products were purified by reverse phase C-18 HPLC and fully characterized by 500 MHz NMR, amino acid analyses, and FAB Mass Spectroscopy.

Catalytic hydrogenolysis with 10% palladium on carbon cleaved the i-Noc protecting groups. After purification by reverse phase HPLC, the cyclic peptides were coupled to an Affi-gel 10 (Bio-Rad) affinity gel generally in accordance with He, et al, *Proc. Natl. Acad. Sci.* (USA), 1989, 86, 1480. To free the $\epsilon$-amino group of Lys$^9$, the affinity gel column was washed with piperidine in DMF. That this procedure was effective could be demonstrated by monitoring the effluents by UV.

EXAMPLE 2

The procedure of Example 1 was repeated, except that structures (7) and (8) were treated with piperidine in methylene chloride to cleave the Fmoc groups.

EXAMPLE 3

Using a procedure generally in accordance with Raynor, et al, *J. Pharmacol. Exp. Ther.*, 1989, 251, 510, the compounds produced in Examples 1 and 2. completely displaced [$^{125}$I] CGP 23996 (des-Ala$^1$, Gly$^2$-desamino-Cys$^3$[Tyr$^{11}$] dicarba$^{3,14}$ somatostatin) from SRIF receptors on membranes of AtT-20 cells with IC$_{50}$ values of 30.1, 2.6, 3.8 and 2.5 nM respectively. By comparison, MK-678 (see, e.g., Veber and Hirschmann, et al., *Life Sciences*, 1984, 34, 1371) had an IC$_{50}$ value of 4.4 nM in this assay.

Those skilled in the art will appreciate that numerous changes and modifications may be made to the preferred embodiments of the invention and that such changes and modifications may be made without departing from the spirit of the invention. For example, the strategy described herein may be useful for the isolation of somatostatin receptors and may also be useful for the selective attachment of other ligands to affinity gels. It is therefore intended that the appended claims cover all such equivalent variations as fall within the true spirit and scope of the invention.

What is claimed is:

1. A compound having structure:

[structure]

wherein:

$R_1$, $R_2$, $R_3$, $R_{4B}$, and $R_6$ are, independently, $(CH_2)_x$—$R_X$ where x is 0 to about 5 and $R_X$ is:

alkyl or alkenyl having from about 1 to about 5 carbon atoms, from 0 to about 3 oxygen atoms, from 0 to about 3 nitrogen atoms, and from 0 to about 3 sulfur atoms;

aryl having about 3 to about 14 carbon atoms, from 0 to about 4 oxygen atoms, from 0 to about 4 nitrogen atoms, and from 0 to about 4 sulfur atoms;

or $NHR_{NP2}$ where $R_{NP2}$ is H or an amine protecting group;

$R_{5B}$ is alkyl or alkenyl having from about 1 to about 14 carbon atoms;

$R_{NP1}$ is H, an amine protecting group, or a solid support; and $R_7$ is H or alkyl having about 1 to about 3 carbon atoms; or $R_6$ and $R_7$ together form a heterocyclic ring having about 4 to about 8 atoms.

2. The compound of claim 1 wherein $R_1$ is hydroxybenzyl.

3. The compound of claim 1 wherein $R_2$ is —$CH_2$-(indole).

4. The compound of claim 1 wherein $R_3$ is —$(CH_2)_4NHR_{WP2}$.

5. The compound of claim 4 wherein $R_{NP2}$ is H or a fluorenylmethoxycarbonyl protecting group.

6. The compound of claim 1 wherein $R_{5B}$ is —$(CH_2)_3$.

7. The compound of claim 6 wherein $R_{NP1}$ is H or an isonicotinyloxycarbonyl protecting group.

8. The compound of claim 1 wherein $R_7$ is H or methyl.

9. The compound of claim 1 having structure:

[structure]

10. The compound of claim 1 having structure:

[structure]

wherein $R_{NP1}$ and $R_{NP2}$ are, independently, H, an amine protecting group, or a solid support.

11. A compound having structure:

[structure]

wherein:

$R_{NP3}$ is H or an amine protecting group;

$R_{CP}$ is H or a carboxyl protecting group;

$R_1$, $R_2$, $R_3$, $R_{4B}$, and $R_6$ are, independently, $(CH_2)_x$—$R_X$ where x is 0 to about 5 and $R_X$ is:

alkyl or alkenyl having from about 1 to about 5 carbon atoms, from 0 to about 3 oxygen atoms, from 0 to about 3 nitrogen atoms, and from 0 to about 3 sulfur atoms;

aryl having about 3 to about 14 carbon atoms, from 0 to about 4 oxygen atoms, from 0 to about 4 nitrogen atoms, and from 0 to about 4 sulfur atoms;

or

NHR$_{NP2}$ where R$_{NP2}$ is H or an amine protecting group;

R$_{5B}$ is alkyl or alkenyl having from about 1 to about 14 carbon atoms;

R$_{NP1}$ is H, an amine protecting group, or a solid support; and

R$_7$ is H or alkyl having about 1 to about 3 carbon atoms; or

R$_6$ and R$_7$ together form a heterocyclic ring having about 4 to about 8 atoms.

12. The compound of claim 11 wherein R$_{NP3}$ is a t-butoxycarbonyl protecting group.

13. The compound of claim 11 wherein R$_{CP}$ is a 2-(trimethylsilyl) protecting group.

14. The compound of claim 11 wherein R$_1$ is hydroxybenzyl.

15. The compound of claim 11 wherein R$_2$ is —CH$_2$-(indole).

16. The compound of claim 11 wherein R$_3$ is —(CH$_2$)$_4$NHR$_{NP2}$.

17. The compound of claim 16 wherein R$_{NP2}$ is a fluorenylmethoxycarbonyl protecting group.

18. The compound of claim 11 wherein R$_{5B}$ is —(CH$_2$)$_3$.

19. The compound of claim 16 wherein R$_{NP1}$ is an isonicotinyloxycarbonyl protecting group.

20. The compound of claim 11 having structure:

21. A compound having structure:

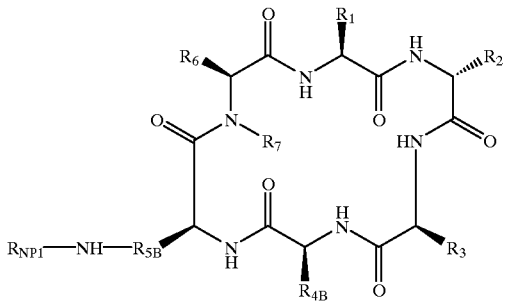

wherein:

R$_1$, R$_2$, R$_3$, and R$_{4B}$ are, independently, (CH$_2$)$_x$—R$_X$ where x is 0 to about 5 and R$_X$ is:

alkyl or alkenyl having from about 1 to about 5 carbon atoms, from 0 to about 3 oxygen atoms, from 0 to about 3 nitrogen atoms, and from 0 to about 3 sulfur atoms;

aryl having about 3 to about 14 carbon atoms, from 0 to about 4 oxygen atoms, from 0 to about 4 nitrogen atoms, and from 0 to about 4 sulfur atoms;

or

NHR$_{NP2}$ where R$_{NP2}$ is H or an amine protecting group;

R$_{5B}$ is alkyl or alkenyl having from about 1 to about 14 carbon atoms;

R$_{NP1}$ is H, an amine protecting group, or a solid support; and

R$_6$ and R$_7$ together form a 5-membered heterocyclic ring.

22. A compound having structure:

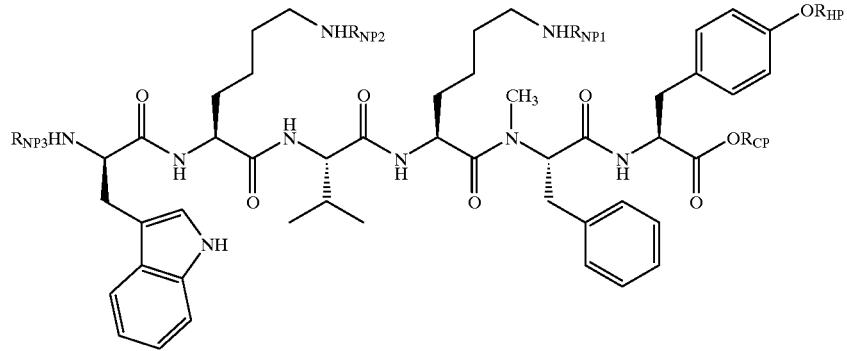

wherein:

R$_{NP3}$ is H or an amine protecting group;

R$_{CP}$ is H or a carboxyl protecting group;

R$_{HP}$ is a hydroxyl protecting group; and

R$_{NP1}$ and R$_{NP2}$ are, independently, H, an amine protecting group, or a solid support.

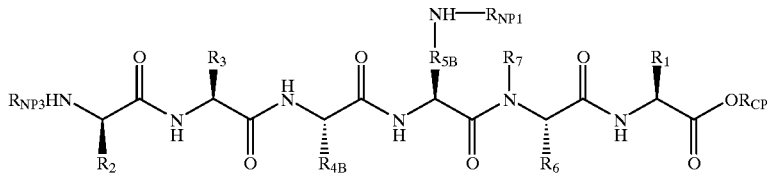

wherein:

$R_{NP3}$ is H or an amine protecting group;

$R_{CP}$ is H or a carboxyl protecting group;

$R_1$, $R_2$, $R_3$, and $R_{4B}$, are, independently, $(CH_2)_x$—$R_X$ where x is 0 to about 5 and $R_X$ is:
  alkyl or alkenyl having from about 1 to about 5 carbon atoms, from 0 to about 3 oxygen atoms, from 0 to about 3 nitrogen atoms, and from 0 to about 3 sulfur atoms;
  aryl having about 3 to about 14 carbon atoms, from 0 to about 4 oxygen atoms, from 0 to about 4 nitrogen atoms, and from 0 to about 4 sulfur atoms;

or $NHR_{NP2}$ where $R_{NP2}$ is H or an amine protecting group;

$R_{5B}$ is alkyl or alkenyl having from about 1 to about 14 carbon atoms;

$R_{NP1}$ is H, an amine protecting group, or a solid support; and $R_6$ and $R_7$ together form a 5-membered heterocyclic ring.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 4
        (B) TYPE: amino acid
        (C) TOPOLOGY: linear (ii) MOLECULE TYPE: peptide (xi) SEQUENCE DESCRIPTION: SEQ ID NO:1:

Phe Trp Lys Thr
 1

(2) INFORMATION FOR SEQ ID NO:2:

(i) SEQUENCE CHARACTERISTICS:
        (A) LENGTH: 6 amino acids
        (B) TYPE: amino acid
        (C) TOPOLOGY: circular (ii) MOLECULE TYPE: peptide (ix) FEATURE:
        (A) NAME/KEY: Modified-site
        (B) LOCATION: 2-3, Xaa at Line 72
        (D) OTHER INFORMATION: /label=protecting1
            /notes-"an amine protecting group or a solid
            support can be present or absent on the primary
            amino group", Xaa=Orn (xi) SEQUENCE DESCRIPTION: SEQ ID NO:2:

Trp Lys Xaa Phe Pro Tyr
 1           5

(2) INFORMATION FOR SEQ ID NO:3:

(i) SEQUENCE CHARACTERISTICS:
        (A) LENGTH: 6
        (B) TYPE: amino acid
        (D) TOPOLOGY: linear (ii) MOLECULE TYPE: peptide (ix) FEATURE:
        (A) NAME/KEY: Modified-site
        (B) LOCATION: 1-3
        (D) OTHER INFORMATION: /label=protecting1
            /note="an amine protecting group or a solid
            support can be present or absent on the primary
            amino group", Xaa: =Orn (ix) FEATURE:
        (A) NAME/KEY: Modified-site
        (B) LOCATION: 6, Xaa at Line 100
        (D) OTHER INFORMATION: /label=protecting2
            /note= "a carboxyl protecting group can be
            present or absent on the hydroxyl group", Xaa=Orn (xi) SEQUENCE DESCRIPTION: SEQ ID NO:3:

Trp Lys Xaa Phe Pro Tyr
 1           5

(2) INFORMATION FOR SEQ ID NO:4:

(i) SEQUENCE CHARACTERISTICS:
        (A) LENGTH: 6

```
            (B) TYPE: amino acid
            (C) TOPOLOGY: linear (ii) MOLECULE TYPE: peptide (ix) FEATURE:
            (A) NAME/KEY: Modified-site
            (B) LOCATION: 1,2,4
            (D) OTHER INFORMATION: /label= protecting1
                /note= "an amine protecting group or a solid
                support can be present or absent on the primary
                amino group"

(ix) FEATURE:
            (A) NAME/KEY: Modified-site
            (B) LOCATION: 5
            (D) OTHER INFORMATION: /label= methyl
                /note= "a methyl group is present on the amino
                group"

(ix) FEATURE:
            (A) NAME/KEY: Modified-site
            (B) LOCATION: 6
            (D) OTHER INFORMATION: /label= protecting3
                /notes= "a hydroxyl protecting group can be
                present or absent on the hydroxyl group"

(xi) SEQUENCE DESCRIPTION: SEQ  ID NO:4:

Trp Lys Val Lys Phe Tyr
 1               5

(2) INFORMATION FOR SEQ ID NO:5:

(i) SEQUENCE CHARACTERISTICS:
            (A) LENGTH: 6
            (B) TYPE: amino acid
            (C) TOPOLOGY: circular (ii) MOLECULE TYPE: peptide (ix) FEATURE:
            (A) NAME/KEY: Modified-site
            (B) LOCATION: 2, 4
            (D) OTHER INFORMATION: /label= protecting1
                /note= "an amine protecting group or a solid
                support can be present or absent on the primary
                amino group"

(ix) FEATURE:
            (A) NAME/KEY: Modified-site
            (B) LOCATION: 5
            (D) OTHER INFORMATION: /label= methyl
                /note= "a methyl group is present on the amino
                group"

(ix) FEATURE:
            (A) NAME/KEY: Modified-site
            (B) LOCATION: 6
            (D) OTHER INFORMATION: /label= protecting3
                /note= "a hydroxyl protecting group can be
                present or absent on the hydroxyl group"

(xi) SEQUENCE DESCRIPTION: SEQ  ID NO:5:

Trp Lys Val Lys Phe Tyr
 1               5
```